(12) United States Patent
Rusin et al.

(10) Patent No.: US 8,317,516 B2
(45) Date of Patent: *Nov. 27, 2012

(54) DENTAL MILL BLANKS

(75) Inventors: Richard P. Rusin, Woodbury, MN (US); Kevin M. Cummings, Little Canada, MN (US); Roger J. Carufel, Marine on St. Croix, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/914,433

(22) Filed: Oct. 28, 2010

(65) Prior Publication Data

US 2011/0045436 A1    Feb. 24, 2011

Related U.S. Application Data

(60) Continuation of application No. 11/834,999, filed on Aug. 7, 2007, now Pat. No. 7,845,947, which is a continuation of application No. 10/027,278, filed on Dec. 21, 2001, now Pat. No. 7,255,562, which is a division of application No. 09/227,230, filed on Jan. 8, 1999, now abandoned.

(51) Int. Cl.
  *A61K 9/08* (2006.01)
(52) U.S. Cl. .................................................. 433/223
(58) Field of Classification Search ............... 433/212.1, 433/213, 223; 264/19
  See application file for complete search history.

(56) References Cited

U.S. PATENT DOCUMENTS

| | | |
|---|---|---|
| 3,066,112 A | 11/1962 | Bowen |
| 3,117,099 A | 1/1964 | Proops |
| 3,179,623 A | 4/1965 | Bowen |
| 3,194,784 A | 7/1965 | Bowen |
| 3,200,142 A | 8/1965 | Bowen |
| 3,729,313 A | 4/1973 | Smith |
| 3,741,769 A | 6/1973 | Smith |
| 3,751,399 A | 8/1973 | Lee, Jr. |
| 3,814,717 A | 6/1974 | Wilson |
| 3,815,239 A | 6/1974 | Lee, Jr. |
| 3,864,426 A | 2/1975 | Salensky |
| 3,926,906 A | 12/1975 | Lee, II |
| 4,129,946 A | 12/1978 | Kennedy |
| 4,250,053 A | 2/1981 | Smith |
| 4,297,266 A | 10/1981 | Ibsen |
| 4,302,381 A | 11/1981 | Omura |
| 4,324,546 A | 4/1982 | Heitlinger |
| 4,394,403 A | 7/1983 | Smith |

(Continued)

FOREIGN PATENT DOCUMENTS

DE    282615    9/1990

(Continued)

OTHER PUBLICATIONS

ASTM Designation: D1208-96, "Standard Test Methods for Common Properties of Certain Pigments", 2007, pp. 1-3.

(Continued)

*Primary Examiner* — Ralph Lewis
(74) *Attorney, Agent, or Firm* — Carlos M. Tellez

(57) ABSTRACT

A dental mill blank including a resin and a filler, wherein the blank is fabricated such that it passes a Thermal Shock Test. The mill blank is substantially free of cracks and discontinuities. Further, the blank may have superior cuttability and hardness.

20 Claims, 1 Drawing Sheet

U.S. PATENT DOCUMENTS

| | | |
|---|---|---|
| 4,411,626 A | 10/1983 | Becker |
| 4,457,714 A | 7/1984 | Klein |
| 4,479,782 A | 10/1984 | Orlowski |
| 4,485,409 A | 11/1984 | Schumacher |
| 4,503,169 A | 3/1985 | Randklev |
| 4,544,359 A | 10/1985 | Waknine |
| 4,547,531 A | 10/1985 | Waknine |
| 4,575,805 A | 3/1986 | Moermann |
| 4,581,389 A | 4/1986 | Schaefer |
| 4,588,756 A | 5/1986 | Bowen |
| 4,615,678 A | 10/1986 | Moermann |
| 4,642,126 A | 2/1987 | Zador |
| 4,652,274 A | 3/1987 | Boettcher |
| 4,695,251 A | 9/1987 | Randklev |
| 4,717,341 A | 1/1988 | Goldberg |
| 4,735,571 A | 4/1988 | Salvo |
| 4,742,464 A | 5/1988 | Duret |
| 4,762,863 A | 8/1988 | Sasaki |
| 4,766,704 A | 8/1988 | Brandestini |
| 4,775,320 A | 10/1988 | Marshall |
| 4,776,704 A | 10/1988 | Kopunek |
| 4,837,732 A | 6/1989 | Brandestini |
| 4,842,454 A | 6/1989 | Gustavsson |
| 4,859,716 A | 8/1989 | Ibsen |
| 4,877,400 A | 10/1989 | Holsclaw |
| 4,894,012 A | 1/1990 | Goldberg |
| 4,970,032 A | 11/1990 | Rotsaert |
| 4,978,640 A | 12/1990 | Kelly |
| 5,027,281 A | 6/1991 | Rekow |
| 5,095,602 A | 3/1992 | Reher |
| 5,098,304 A | 3/1992 | Scharf |
| 5,106,303 A | 4/1992 | Oden |
| 5,108,002 A | 4/1992 | Rowan |
| 5,120,224 A | 6/1992 | Golub |
| 5,135,393 A | 8/1992 | Eidenbenz |
| 5,151,044 A | 9/1992 | Rotsaert |
| 5,182,332 A | 1/1993 | Yamamoto |
| 5,224,049 A | 6/1993 | Mushabac |
| 5,276,068 A | 1/1994 | Waknine |
| 5,330,353 A | 7/1994 | Wavrin |
| 5,332,429 A | 7/1994 | Mitra |
| 5,342,194 A | 8/1994 | Feldman |
| 5,342,201 A | 8/1994 | Oden |
| 5,342,696 A | 8/1994 | Eidenbenz |
| 5,354,785 A | 10/1994 | Rheinberger |
| 5,356,951 A | 10/1994 | Yearn |
| 5,360,482 A | 11/1994 | Belvedere |
| 5,362,769 A | 11/1994 | Waller |
| 5,383,752 A | 1/1995 | Rheinberger |
| 5,444,104 A | 8/1995 | Waknine |
| 5,462,791 A * | 10/1995 | Kashima et al. .............. 442/212 |
| 5,545,039 A | 8/1996 | Mushabac |
| 5,545,676 A | 8/1996 | Palazzotto |
| 5,564,929 A | 10/1996 | Alpert |
| 5,676,745 A | 10/1997 | Kelly |
| 5,684,103 A | 11/1997 | Jia |
| 5,691,905 A | 11/1997 | Dehoff |
| 5,772,438 A | 6/1998 | Deom |
| 5,775,911 A | 7/1998 | Hahn |
| 5,797,748 A | 8/1998 | Reynaud |
| 5,813,859 A | 9/1998 | Hajjar |
| 5,816,816 A | 10/1998 | Scharf |
| 5,823,778 A | 10/1998 | Schmitt |
| 5,846,640 A | 12/1998 | Vallittu |
| 5,869,548 A | 2/1999 | Ikushima |
| 5,921,778 A | 7/1999 | Karmaker |
| 5,939,211 A | 8/1999 | Mörmann |
| 5,969,000 A | 10/1999 | Yang |
| 5,980,253 A | 11/1999 | Oxman |
| 5,990,195 A | 11/1999 | Arita |
| 5,998,495 A | 12/1999 | Oxman |
| 6,013,694 A | 1/2000 | Jia |
| 6,025,406 A | 2/2000 | Oxman |
| 6,030,220 A | 2/2000 | Karmaker |
| 6,030,606 A | 2/2000 | Holmes |
| 6,039,569 A | 3/2000 | Prasad |
| 6,043,295 A | 3/2000 | Oxman |
| 6,049,743 A | 4/2000 | Baba |
| 6,186,790 B1 | 2/2001 | Karmaker |
| 6,187,833 B1 | 2/2001 | Oxman |
| 6,187,836 B1 | 2/2001 | Oxman |
| 6,287,121 B1 | 9/2001 | Guiot |
| 6,345,984 B2 | 2/2002 | Karmaker |
| 6,379,593 B1 | 4/2002 | Datzmann |
| 6,403,676 B1 | 6/2002 | Jia |
| 7,255,562 B2 * | 8/2007 | Rusin et al. .................... 433/223 |
| 7,845,947 B2 * | 12/2010 | Rusin et al. .................... 433/223 |
| 2001/0036617 A1 | 11/2001 | Karmaker |
| 2002/0076530 A1 | 6/2002 | MacDougald |
| 2002/0086266 A1 | 7/2002 | Karmaker |

FOREIGN PATENT DOCUMENTS

| | | |
|---|---|---|
| EP | 295627 | 12/1988 |
| EP | 614344 | 6/1993 |
| EP | 701808 | 3/1996 |
| EP | 742001 | 11/1996 |
| EP | 803241 | 10/1997 |
| EP | 850601 | 7/1998 |
| EP | 870479 | 10/1998 |
| EP | 913130 | 5/1999 |
| EP | 1062916 | 12/2000 |
| GB | 1428454 | 3/1976 |
| GB | 2079297 | 1/1982 |
| GB | 2291053 | 1/1996 |
| JP | 0355212 | 3/1991 |
| JP | 0825502 | 1/1996 |
| JP | 0949925 | 2/1997 |
| JP | 9238957 | 9/1997 |
| JP | 2000107203 | 4/2000 |
| WO | WO 91/07139 | 5/1991 |
| WO | WO 94/08783 | 4/1994 |
| WO | WO 96/37163 | 11/1996 |
| WO | WO 98/46197 | 10/1998 |
| WO | WO 02/11678 | 2/2002 |

OTHER PUBLICATIONS

Ellis, ed., Chemistry and Technology of Epoxy Resins, Chapman & Hall, 7 pages, (1993).
Jeneric®IPentron®, Incorporated, Product Catalog, Wallingford, CT, Mar. 2000, 4 pages.
<http://www.denovodental.comldvomatrx.htm>, Mar. 13, 2001, 1 page.
<http://www.pulpdenL.comfbonding/hc.html>, Mar. 12, 2001, 2 pages.
Mann, Electrochemical Reactions in Nonaqueous Systems, Marcel Dekker, Inc., New York, pp. 8-9, (1970).
Scaiano, ed., CRC Handbook of Organic Photochemistry, vol. II, pp. 335-339, (1989).
U.S. Appl. No. 09/227,230, (Dental Mill Blanks), now abandoned.
Webster's II New College Dictionary, p. 119, (1995).
Weinburg, ed., Technique of Electroorganic Synthesis Part II Techniques of Chemistry, vol. V, pp. 8, (1975).

* cited by examiner

DENTAL MILL BLANKS

CROSS REFERENCE TO RELATED APPLICATIONS

This application is a continuation of U.S. patent application Ser. No. 11/834,999, filed Aug. 7, 2007 now U.S. Pat. No. 7,845,947, which is a continuation of U.S. patent application Ser. No. 10/027,278, now U.S. Pat. No. 7,255,562, filed Dec. 21, 2001, which is a division of U.S. patent application Ser. No. 09/227,230, now abandoned, filed Jan. 8, 1999, all of which are incorporated in their entirety herein.

FIELD OF THE INVENTION

This invention is related to polymeric based mill blanks that are substantially free of cracks and are suitable for use in fabricating dental and medical prostheses by CAD/CAM (computer-aided design/computer-aided machining) procedures.

BACKGROUND OF THE INVENTION

The art of fabricating custom-fit prosthetics in the medical and dental fields is well-known. Prosthetics are replacements for tooth or bone structure; examples include restoratives, replacements, inlays, onlays, veneers, full and partial crowns, bridges, implants, posts, etc. Currently, most prostheses in dentistry are either made by hand by a dental practitioner while the patient is in the dental chair, or by an independent laboratory who is capable of such fabrication.

Materials used to make the prostheses typically include gold, ceramics, amalgam, porcelain and composites. For dental restorative work such as fillings, amalgam is a popular choice for its long life and low cost. Amalgam also provides a dental practitioner the capability of fitting and fabricating a dental filling during a single session with a patient. The aesthetic value of amalgam, however, is quite low, as its color drastically contrasts to that of natural teeth. For large inlays and fillings, gold is often used. However, similar to amalgam, gold fillings contrast to natural teeth hues. Thus, dental practitioners are increasingly turning to ceramic or polymer-ceramic composite materials whose color can be matched with that of the tooth.

The conventional procedure for producing dental prosthetics typically requires the patient to have at least two sessions with the dentist. First, an impression is taken of the dentition using an elastomeric material from which a cast model is made to replicate the dentition. The prosthetic is then produced from the model using metal, ceramic or a composite material. A series of steps for proper fit and comfort then follows. Thus, fabrication of custom prostheses involves intensive labor, a high degree of skill and craftsmanship, and lengthy times (1-2 days). Alternatively, a practitioner may opt for a sintered metal system that may be faster. However, those procedures are still labor intensive and complicated.

In recent years, technological advances have provided computer automated machinery capable of fabricating prostheses using minimal human labor and drastically lower work time. This is frequently referred to as "digital dentistry," where computer automation is combined with optics, digitizing equipment, CAD/CAM (computer-aided design/computer aided machining) and mechanical milling tools. Examples of such a computer-aided milling machine include the CEREC 2™ machine supplied by Siemens (available from Sirona Dental Systems; Bensheim, Germany) VITA CELAY™, (available from Vita Zahn Fabrik; Bad Sackingen, Germany) PRO-CAM™ (Intra-Tech Dental Products, Dallas, Tex.) and PROCERA ALLCERAM™ (available from Nobel Biocare USA, Inc.; Westmont, Ill.). U.S. Pat. Nos. 4,837,732, 4,575,805 and 4,776,704 also disclose the technology of computer-aided milling machines for making dental prostheses. These machines produce dental prostheses by cutting, milling, and grinding the near-exact shape and morphology of a required restorative with greater speed and lower labor requirements than conventional hand-made procedures.

Fabrication of a prostheses using a CAD/CAM device requires a "mill blank," a solid block of material from which the prosthetic is cut or carved. The mill blank is typically made of ceramic material. U.S. Pat. No. 4,615,678 discloses a blank adapted for use in machine fabrication of dental restorations comprising a ceramic silica material. There exist various mill blanks available commercially, including VITA CELAY™ porcelain blanks Vita Mark II Vitablocks™ and VITA IN-CERAM™ ceramic blanks (both available from Vita Zahn Fabrik; Bad Sackingen, Germany). Machinable micaceous ceramic blanks (e.g. Corning MACOR™ blanks and Dentsply DICOR™) are also known in the art.

SUMMARY OF THE INVENTION

The invention provides mill blanks for making dental prosthetics comprising a polymeric resin and a filler, wherein the mill blank is substantially free of cracks, or fissures, and able to withstand a Thermal Shock Test, a test that exposes the existence of internal stresses in the mill blank, which can lead to cracking of the material before or during the milling operation or during clinical use of the ultimate prosthesis. Preferably, the mill blank of the present invention is also substantially free of material discontinuities larger than about 1 millimeter. The mill blank's surprising ability to pass a Thermal Shock Test is a result of the relief of stress created during the curing process or proper low stress curing wherein little or no stress is actually created in the blank. Preferably low stress cure is performed by slow light curing methods. Heat treatment following a fast cure has also been surprisingly found to minimize internal stresses and provide the mill blank the same ability to pass the Thermal Shock Test.

By careful selection of the resin and filler, additional desirable material properties may be achieved, including superior cuttability and hardness over commercially available blanks Preferred resins are free radically curable, cationically curable, or a combination thereof. Preferred fillers for the invention are those that have been derived by sol-gel process.

DESCRIPTION OF THE INVENTION

Figure 1:
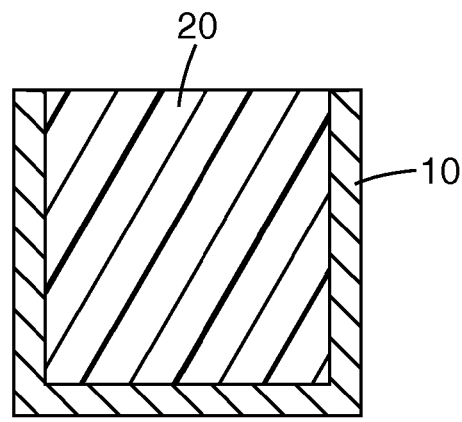
FIG. 1 is a side cross-sectional view of an exemplary embodiment of a mill blank and an exemplary embodiment of a mold for making the same.
Figure 2:
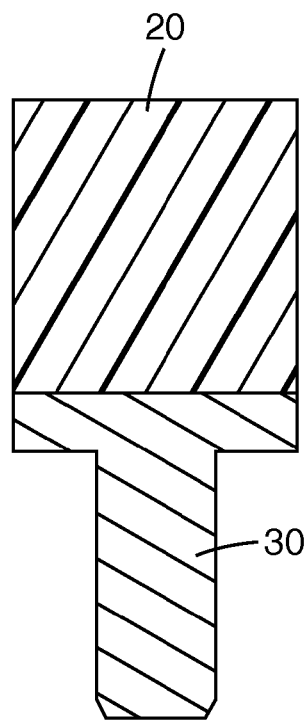
FIG. 2 is a side cross-sectional view of an exemplary embodiment of a mill blank having a handle attached thereto.

Physical properties such as hardness and brittleness of ceramics limit the usefulness as dental prosthetics. Metals also have their shortcomings, as they are not aesthetic and may cause concern regarding allergic reactions and the like. Thus, it would be advantageous to have a prosthetic made from a strong and durable material, where the material would be suitable for use in simple and economical devices such as existing CAD/CAM manufacturing equipment.

The present invention focuses on mill blanks made of highly filled composite material, suitable for use in fabricating dental prostheses, preferably using precision manufacturing equipment, such as CAD/CAM milling devices.

The blanks of the present invention display excellent performance in many characteristics important for dental or medical use, including compressive strength, diametral tensile strength, flexural strength, fracture toughness, hardness, resistance to wear, wear on opposing dentition, durability, polishability, polish retention, esthetics, thermal expansion, visual opacity, x-ray opacity, impact strength, chemical durability, biocompatibility, modulus, shelf life, patient comfort, ease-of-use, and structural integrity.

A "composite" material refers to a hardenable (or hardened) composition containing at least in part, a polymerizable (or polymerized) resin(s), filler particles of one or more types, a polymerization initiator, and any desired adjuvants. Composites of the present invention can be multiple- or one-part compositions where polymerization may be initiated by a variety of means including heat, light, radiation, e-beam, microwave, or chemical reaction.

It has been surprisingly found that a mill blank made of composite material provides certain advantages and appealing features over ceramic and porcelain blanks Careful selection of the combination of the components provides improved cuttability performance. "Cuttability", as used herein, is a property of a mill blank of the present invention, characterized by how well a blank responds to contact from a cutting tool. For example, a measurement may be performed by measuring the depth of a cut made by a cutting tool when the tool is applied with a constant force for a fixed period of time. Preferably, the cuttability value of a mill blank is established by a standard test described herein, where the Cuttability Value is determined by comparison to a standard material.

It has also been surprisingly found that careful selection of the resin, filler and adjuvants provides an advantageous capability of the composite to be loaded with substantially high amounts of filler. This filler loading translates into improved durability, wear, and hardness of the composite mill blank. The addition of filler to a composition provides desirable levels of viscosity for material processing and strength for durability of the finished product. "Wear", as used herein, is also a property of a mill blank of the present invention that can be characterized by compressive strength and diametral tensile strength. Hardness can be characterized by a Barcol Hardness measurement. It is desirable for a dental prosthetic to have a high resistance to wear and a high degree of hardness in order for it to maintain its intended shape and integrity as well as be useful in the oral environment. However, it is also desirable that the prosthetic material not unduly wear opposing or surrounding dentition.

A further advantage the present invention has over ceramic mill blanks is the ease of finishing. A practitioner would have the ability, if necessary, to repair or modify a prosthetic made from the present invention's composite composition much more easily than if the repair had to be made on a ceramic or porcelain prosthetic. Ideally, like materials would be used to repair a prosthetic in the oral environment, materials appropriate for repairing the instant prosthetic may be cured by radiant energy within the oral environment. In contrast, ceramics require firing and sintering at extremely high temperatures (typically greater than 700° C.) and therefore a repair material made of ceramic is not useful in the mouth.

The polymeric resin and filler of the present invention are preferably selected such that the resulting mill blank has a Barcol Hardness that is greater than or equal to the Barcol Hardness of a Fumed Silica Mill Blank Standard. More preferably, the mill blank has a Barcol Hardness that is about 5% greater than the Barcol Hardness of a Fumed Silica Mill Blank Standard, and most preferably about 15% greater. Preferably, the polymeric resin and filler of the present invention are selected such that the Cuttability Value is about 30% greater than the Cuttability Value of a Fumed Silica Mill Blank Standard, more preferably 50% greater, and most preferably 100% greater. The Fumed Silica Mill Blank Standard is a mill blank made from bis-GMA TEGDMA resin loaded with silane treated fumed silica filler, such as the filler available under the trade name AEROSIL OX50 (Degussa Corporation, Pigments Division, Teterboro, N.J.). The fumed silica filler has an average primary particle size of 40 nanometers (nm), a surface area of 50±15 $m^2/g$ as measured by DIN 66131, pH value of 3.7-4.7 via ASTM D1208, purity of greater than 99.8% $SiO_2$ and has a tap density of approximately 130 gaper ISO 787/x1 synthesized via continuous flame hydrolysis of $SiCl_4$.

As used herein, "curable" and "polymerizable" are used interchangeably.

Polymerizable resins suitable for use in the dental composite mill blank of the present invention are hardenable organic resins having sufficient strength, hydrolytic stability, and non-toxicity to render them suitable for use in the oral environment. Preferably, the resin is made from a material comprising a free radically curable monomer, oligomer, or polymer, or a cationically curable monomer, oligomer, or polymer, or both. Alternatively, the resin may be made from a material comprising a monomer, oligomer or polymer comprising both a free radically curable functionality and a cationically curable functionality.

A particularly preferred polymerizable resin for use in the present invention is a mixture of two free radically curable monomers, namely, diglycidylmethacrylate of Bisphenol A (frequently referred to as "Bis-GMA") and triethyleneglycol dimethacrylate (frequently referred to as "TEGDMA"). Such a material is available commercially under the trade name 3M Restorative™ Z100 (3M Co., St. Paul, Minn.). This particular resin creates unexpectedly preferred cutting and milling characteristics during the production of a dental prosthetic.

Other preferred polymerizable resins containing free radically curable functionalities include acrylates and methacrylates commonly used in contemporary dental composites e.g. 2,2-bis[4-(2-hydroxy-3-methacryloyloxypropoxy)phenyl] propane (bisGMA); triethyleneglycol dimethacrylate (TEGDMA); 2,2-bis[4-(2-methacryloyloxyethoxy)-phenyl] propane (bisEMA); 2-hydroxy ethyl methacrylate (HEMA); urethane dimethacrylate (UDMA) and combinations thereof.

Resins made from cationically curable material suitable for use in the present invention include epoxy resins. Epoxy resins impart high toughness to composites, a desirable feature for composite mill blanks Epoxy resins may optionally be blended with various combinations of polyols, methacrylates, acrylates, or vinyl ethers. Preferred epoxy resins include diglycidyl ether of bisphenol A (e.g. EPON 828, EPON 825; Shell Chemical Co.), 3,4-epoxycyclohexylmethyl-3-4-epoxy cyclohexene carboxylate (e.g. UVR-6105, Union Carbide), bisphenol F epoxides (e.g. GY-281; Ciba-Geigy), and polytetrahydrofuran.

As used herein, "cationically active functional groups" is a chemical moiety that is activated in the presence of an initiator capable of initiating cationic polymerization such that it is available for reaction with other compounds bearing cationically active functional groups. Materials having cationically active functional groups include cationically polymerizable epoxy resins. Such materials are organic compounds having an oxirane ring, i.e., a group of the formula

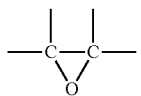

which is polymerizable by ring opening. These materials include monomeric epoxy compounds and epoxides of the polymeric type and can be aliphatic, cycloaliphatic, aromatic or heterocyclic. These materials generally have, on the average, at least 1 polymerizable epoxy group per molecule, preferably at least about 1.5 and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Useful epoxy-containing materials include those which contain cyclohexane oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl) adipate. For a more detailed list of useful epoxides of this nature, reference is made to the U.S. Pat. No. 3,117,099, which is incorporated herein by reference.

Blends of various epoxy-containing materials are also contemplated. Examples of such blends include two or more weight average molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical natures, such as aliphatic and aromatic, or functionalities, such as polar and non-polar. Other types of useful materials having cationically active functional groups include vinyl ethers, oxetanes, spiro-orthocarbonates, spiro-orthoesters, and the like.

The resin may be chosen from acrylate-based compositions that contain a free radically active functional group. Materials having free radically active functional groups include monomers, oligomers, and polymers having one or more ethylenically unsaturated groups. As used herein, "free radically active functional group" is a chemical moiety that is activated in the presence of an initiator capable of initiating free radical polymerization such that it is available for reaction with other compounds bearing free radically active functional groups. Suitable materials contain at least one ethylenically unsaturated bond, and are capable of undergoing addition polymerization. Such free radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, and trihydroxyethyl-isocyanurate trimethacrylate; the bis-acrylates and bis-methacrylates of polyethylene glycols of molecular weight 200-500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

If desired, both cationically active and free radically active functional groups may be contained in a single molecule. Such molecules may be obtained, for example, by reacting a di- or poly-epoxide with one or more equivalents of an ethylenically unsaturated carboxylic acid. An example of such a material is the reaction product of UVR-6105 (available from Union Carbide) with one equivalent of methacrylic acid. Commercially available materials having epoxy and free-radically active functionalities include the "Cyclomer" series, such as Cyclomer M-100, M-101, or A-200 available from Daicel Chemical, Japan, and Ebecryl-3605 available from Radcure Specialties.

The resin can also include an acid functionality, such as carboxylic acid, phosphoric and phosphonic acids. Examples of such compounds include the aliphatic carboxy compounds, such as acrylic acid, methacrylic acid, maleic acid, fumaric acid, itaconic acid, crotonic acid, aconitic acid, glutaconic acid, mesaconic acid, citraconic acid, acid, tiglicinic acid, 2-chloroacrylic acid, 3-chloroacrylic acid, 2-bromoacrylic acid, 1-methacryloyl malonic acid, 1-acryloyl malic acid, N-methacryloyl and N-acryloyl derivatives of amino acids, and acids such as tartaric acid, citric acid, malic acid that have been further functionalized with an ethylenic functionality. For example, citric acid may be ethylenically functionalized by substituting with an acryloyl or methacryloyl functionality. These polymerizable groups may be attached directly to the acid containing compound, or may be optionally attached through a linking group. Preferred linking groups include substituted or unsubstituted alkyl, alkoxyalkyl, aryl, aryloxyalkyl, alkoxyaryl, aralkyl or alkaryl groups. Particularly preferred linking groups comprise an ester functionality and most particularly preferred linking groups comprise an amide functionality.

Polymeric initiator systems for the above resins would no longer be limited to systems which are compatible with the oral environment as the bulk of the polymerization of the resin constituents would occur outside of the patient's mouth, such as in a manufacturing facility where the mill blanks may be produced. Thus, many of the commonly known polymerization systems may be employed, such as curing systems involving 2-part resins, heat, radiation, redox reactions or combinations thereof. By having the capability of employing various polymerization systems, waiting time for the patient is drastically reduced, as those particular steps would be completed in the manufacturing site or laboratory. However, since a composite mill blank provides a practitioner the opportunity to finish a prosthetic at chairside (i.e while the patient waits), it is preferred that polymeric initiator systems that are compatible with the oral environment are employed.

One class of useful initiators includes sources of species capable of initiating both free radical and cationic polymerization.

Preferred free radical polymerization systems contain three components: an onium salt, a sensitizer, and a free radical donor. Suitable salts include mixed ligand arene cyclopentadienyl metal salts with complex metal halide ions, as described in "CRC Handbook of Organic Photochemistry", vol II, ed. J. C. Scaiano, pp. 335-339 (1989). Preferably, the source is an onium salt such as a sulfonium or iodonium salt. Of the onium salts, iodonium salts (e.g., aryl iodonium salts) are particularly useful. The iodonium salt should be soluble in the composition and preferably is shelf-stable, meaning it does not spontaneously promote polymerization when dissolved therein in the presence of the cationic polymerization modifier and photosensitizer (if included). Accordingly, selection of a particular iodonium salt may depend to some extent upon the particular polymerizable reactants, cationic polymerization modifiers, and sensitizers (if included).

Suitable iodonium salts are described in U.S. Pat. Nos. 3,729,313; 3,741,769; 4,250,053; 4,394,403; and 5,545,676, the disclosures of which are incorporated herein by reference. The iodonium salt can be a simple salt, containing an anion such as $Cl^-$, $Br^-$, $I^-$, $C_4H_5SO_3^-$, or $C(SO_2CF_3)_3^-$; or a metal complex salt containing an antimonate, arsenate, phosphate, or borate such as $SbF_5OH^-$, $AsF_6^-$, or $B(C_6F_5)_4^-$. Mixtures of iodonium salts can be used if desired.

The initiation system may also include a sensitizer such as a visible light sensitizer that is soluble in the polymerizable composition. The sensitizer preferably is capable of absorbing light having wavelengths in the range from about 300 to about 1000 nanometers.

Examples of suitable sensitizers include ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes, and pyridinium dyes. Ketones (e.g., monoketones or alpha-diketones), ketocoumarins, aminoarylketones, and p-substituted aminostyryl ketone compounds are preferred sensitizers. For applications requiring deep cure of epoxy-containing materials (e.g., cure of highly filled composites), it is preferred to employ sensitizers having an extinction coefficient below about 100 $lmole^{-1}$ $cm^{-1}$, more preferably about or below 100 $lmole^{-1}$ $cm^{-1}$, at the desired wavelength of irradiation for photopolymerization. The alpha-diketones are an example of a class of sensitizers having this property, and are particularly preferred for dental applications.

Examples of particularly preferred visible light sensitizers include camphorquinone; glyoxal; biacetyl; 3,3,6,6-tetramethylcyclohexanedione; 3,3,7,7-tetramethyl-1.2-cycloheptanedione; 3,3,8,8-tetramethyl-1,2-cyclooctanedione; 3,3,18,18-tetramethyl-1,2-cyclooctadecanedione; dipivaloyl; benzil; furil; hydroxybenzil; 2,3-butanedione; 2,3-pentanedione; 2,3-hexanedione; 3,4-hexanedione; 2,3-heptanedione; 3,4-heptanedione; 2,3-octanedione; 4,5-octanedione; and 1,2-cyclohexanedione; Of these, camphorquinone is the most preferred sensitizer.

The third component in the free radical polymerization system is the electron donor. A wide variety of donors can be employed. The donor is soluble in the resin component of the mill blank processor and should meet the oxidation potential ($E_ox$) limitation discussed in more detail below. Preferably, the donor also is selected based in part upon shelf stability considerations. Accordingly, a selection of a particular donor may depend in part on the resin component, iodonium salt and sensitizer chosen. Suitable donors are capable of increasing the speed of cure or depth of cure of a composition of the invention upon exposure to light of the desired wavelength. Also, the donor has an $E_ox$ greater than zero and less than or equal to $E_ox$ (p-dimethoxybenzene). Preferably $E_ox$ (donor) is between about 0.5 and 1 volts against a saturated calomel electrode. $E_ox$ (donor) values can be measured experimentally, or obtained from references such as N. L. Weinburg, Ed., Technique of Electroorganic Synthesis Part II Techniques of Chemistry, Vol. V (1975), and C. K. Mann and K. K. Barnes, Electrochemical Reactions in Nonaqueous Systems (1970).

In the cases where cationic polymerization occurs, it may be desirable to delay the onset of polymerization. For example, in the case of a hybrid composition that includes both free radically active functional groups and cationically active functional groups, it may be desirable to use an initiation system suitable for initiating both free radical and cationic polymerization which is designed such that for a given reaction temperature, photoinitiation of free radical polymerization occurs after a finite induction period $T_1$ and photoinitiation of cationic polymerization occurs after a finite induction period $T_3$, where $T_3$ is greater than $T_1$. $T_1$ and $T_3$ are measured relative to administration of the first dose of actinic radiation which occurs at $T_0$. Such initiation systems are described in Oxman et al., "Compositions Featuring Cationically Active and Free Radically Active Functional Groups, and Methods for Polymerizing Such Compositions," filed Jun. 5, 1998 and bearing U.S. Ser. No. 09/092,550, which is assigned to the same assignee as the present application and hereby incorporated by reference. As described therein, the photoinitiation system includes: (i) a source of species capable of initiating free radical polymerization of the free radically active functional group and cationic polymerization of the cationically active functional group; and (ii) a cationic polymerization modifier. The amount and type of modifier are selected such that in the absence of the modifier, initiation of cationic polymerization under the same irradiation conditions occurs at the end of a finite induction period $T_2$ (also measured relative to $T_0$), where $T_2$ is less than $T_3$.

The induction periods ($T_1$, $T_2$, and $T_3$) can be measured using differential scanning calorimetry. Following the first irradiation event at $T_0$, the enthalpy of the reaction is measured as a function of time. Both initiation of free radical polymerization and initiation of cationic polymerization result in an increase in enthalpy, observed as a pair of separate peaks when data is charted on a graph. The time at which initiation occurs is taken to be the time at which the enthalpy begins to rise.

The cationic polymerization modifier preferably has a photoinduced potential less than that of 3-dimethylaminobenzoic acid in a standard solution of $2.9 \times 10^{-5}$ moles/g diphenyliodonium hexafluoroantimonate and $1.5 \times 10^{-5}$ moles/g camphorquinone in 2-butanone, measured according to the procedure described in the aforementioned Oxman et al. application. In general, useful cationic polymerization modifiers are typically bases having $pK_b$ values, measured in aqueous solution, of less than 10. Examples of classes of suitable cationic polymerization modifiers include aromatic amines, aliphatic amines, aliphatic amides, aliphatic ureas; aliphatic and aromatic phosphines, and salts of organic or inorganic acids (e.g., salts of sulfinic acid). Specific examples include 4-(dimethylamino)phenylacetic acid, dimethylaminophenethanol, dihydroxy p-toluidine, N-(3,5-dimethylphenyl)-N,N-diethanolamine, 2,4,6-pentamethylaniline, dimethylbenzylamine, N,N-dimethylacetamide, tetramethylurea, N-methyldiethanolamine, triethylamine, 2-(methylamino)ethanol, dibutylamine, diethanolamine, N-ethylmorpholine, trimethyl-1,3-propanediamine, 3-quinuclidinol, triphenylphosphine, sodium toluene sulfinate, tricyclohexylphosphine, N-methylpyrollidone, and t-butyldimethylaniline. These modifiers may be used alone or in combination with each other, or with a material having photoinduced potential greater than that of 3-dimethylaminobenzoic acid in a standard solution of $2.9 \times 10^{-5}$ moles/g diphenyliodonium hexafluoroantimonate and $1.5 \times 10^{-5}$ moles/g camphorquinone in 2-butanone; an example of such a material is ethyl 4-(dimethylamino)benzoate ("EDMAB").

In other cases, it may be desirable to accelerate initiation of cationic polymerization. For example, in certain hybrid compositions it may be desirable to achieve near-simultaneous initiation of the free radically active functional groups and the cationically active functional groups. Examples of suitable initiation systems for accomplishing this objective are described in Oxman et al., U.S. Ser. No. 08/838,835 filed Apr. 11, 1997 entitled "Ternary Photoinitiator System for Curing of Epoxy/Polyol Resin Compositions" and Oxman et al., U.S. Ser. No. 08/840,093 filed Apr. 11, 1997 entitled "Ternary Photoinitiator System for Curing of Epoxy Resins," both of which are assigned to the same assignee as the present application and hereby incorporated by reference. As described therein, the photoinitiator system includes an iodonium salt (e.g., an aryliodonium salt), a visible light sensitizer (e.g., camphorquinone), and an electron donor. The systems have a photoinduced potential greater than or equal to that of 3-dimethylaminobenzoic acid in a standard solution of $2.9 \times 10^{-5}$ moles/g diphenyliodonium hexafluoroantimonate and $1.5 \times 10^{-5}$ moles/g camphorquinone in 2-butanone, measured according to the procedure described in the aforementioned Oxman et al. applications. An example of a suitable electron donor is ethyl 4-(dimethylamino)benzoate ("EDMAB").

In the case of hybrid compositions that include both free radically active functional groups and cationically active functional groups, it may be desirable to use one initiation system for free radical polymerization and a separate initiation system for cationic polymerization. The free radical polymerization initiation system is selected such that upon activation, only free radical polymerization is initiated.

One class of initiators capable of initiating polymerization of free radically active functional groups, but not cationically active functional groups, includes conventional chemical initiator systems such as a combination of a peroxide and an amine. These initiators, which rely upon a thermal redox reaction, are often referred to as "auto-cure catalysts." They are typically supplied as two-part systems in which the reactants are stored apart from each other and then combined immediately prior to use.

A second class of initiators capable of initiating polymerization of free radically active functional groups, but not cationically active functional groups, includes free radical-generating photoinitiators, optionally combined with a photosensitizer or accelerator. Such initiators typically are capable of generating free radicals for addition polymerization at some wavelength between 200 and 800 nm. Examples include alpha-diketones, monoketals of alpha-diketones or ketoaldehydes, acyloins and their corresponding ethers, chromophore-substituted halomethyl-s-triazines, and chromophore-substituted halomethyl-oxadiazoles.

A third class of initiators capable of initiating polymerization of free radically active functional groups, but not cationically active functional groups, includes free radical-generating thermal initiators. Examples include peroxides and azo compounds such as azobisisobutyronitrile (AIBN). A preferred thermal initiator is benzoyl peroxide.

Dual initiation systems include a separate photoinitiation system for initiating polymerization of the cationically active functional groups. The cationic initiation system is selected such that activation of the free radical initiation system does not activate the cationic initiation system. Examples of suitable cationic photoinitiation systems for a dual initiation system composition include the onium salts and mixed ligand arene cyclopentadienyl metal salts with complex metal halide ions described above. Also suitable are cationic initiators that are activated by heat, or part cationic initiators. Such systems are described in "Chemistry and Technology of Epoxy Resins," ed. by B. Ellis, Chapman & Hall, 1993.

A filler for the present invention is preferably a finely divided material that may optionally have an organic coating. Suitable coatings include silane or encapsulation in a polymeric matrix.

Fillers may be selected from one or more of any material suitable for incorporation in compositions used for medical applications, such as fillers currently used in dental restorative compositions and the like. The filler is finely divided and preferably has a maximum particle diameter less than about 50 micrometers and an average particle diameter less than about 10 micrometers. The filler can have a unimodal or polymodal (e.g., bimodal) particle size distribution. The filler can be an inorganic material. It can also be a crosslinked organic material that is insoluble in the polymerizable resin, and is optionally filled with inorganic filler. The filler should in any event be non-toxic and suitable for use in the mouth. The filler can be radiopaque, radiolucent or non-radiopaque.

Examples of suitable inorganic fillers are naturally-occurring or synthetic materials such as quartz, nitrides (e.g., silicon nitride); glasses containing, for example Ce, Sb, Sn, Zr, Sr, Ba, An, La, Y and Al; colloidal silica; feldspar; borosilicate glass; kaolin; talc; titania; and zinc glass; low Mohs hardness fillers such as those described in U.S. Pat. No. 4,695,251; and submicron silica particles (e.g., pyrogenic silicas such as the "Aerosil" Series "OX 50", "130", "150" and "200" silicas sold by Degussa and "Cab-O-Sil M5" silica sold by Cabot Corp.). Examples of suitable organic filler particles include filled or unfilled pulverized polycarbonates, polyepoxides, polyaramid, and the like. Preferred filler particles are quartz, barium glass, and non-vitreous microparticles of the type described in U.S. Pat. No. 4,503,169. Metallic fillers may also be incorporated, such as particulate metal filler made from a pure metal such as those of Groups IVA, VA, VIA, VIIA, VIII, IB, or IIB, aluminum, indium, and thallium of Group IIIB, and tin and lead of Group IVB, or alloys thereof. Conventional dental amalgam alloy powders, typically mixtures of silver, tin, copper, and zinc, may also optionally be incorporated. The particulate metallic filler preferably has an average particle size of about 1 micron to about 100 microns, more preferably 1 micron to about 50 microns. Mixtures of these fillers are also contemplated, as well as combination fillers made from organic and inorganic materials. Fluoroaluminosilicate glass fillers, either untreated or silanol treated, are particularly preferred. These glasses have the added benefit of releasing fluoride at the site of dental work when placed in the oral environment.

Optionally, the surface of the filler particles may be treated with a surface treatment such as a coupling agent in order to enhance the bond between the filler and the polymerizable resin. The coupling agent may be functionalized with reactive curing groups, such as acrylates, methacrylates, epoxies, and the like. Examples of coupling agents include gamma-methacryloxypropyltrimethoxysilane, gamma-mercaptopropyltriethoxysilane, gamma-aminopropyltrimethoxysilane, beta-(3,4-epoxycyclohexyl)ethyl-trimethoxysilane, gamma-glycidoxypropyltrimethoxysilane, and the like.

Preferable fillers are those that have been derived through sol-gel processes. It has been surprisingly found that sol-gel derived fillers impart superior machining characteristics to composites used for dental mill blanks. Moreover, it was surprisingly found that sol-gel derived fillers may be incorporated into resins at higher levels than conventional milled glass fillers. Sol-gel processes for making fillers are described, for example, in U.S. Pat. No. 4,503,169 (Randklev) and by Noritake et al. in GB Patent 2291053B. As used herein, "sol-gel" refers to any method of synthesizing inorganic particles that comprises a step wherein at least one of the precursors is an aqueous or organic dispersion, sol, or solution.

A preferred method for preparing the sol-gel derived microparticles or fillers for the present invention involves the combining of (1) an aqueous or organic dispersion or sol of amorphous silica with (2) an aqueous or organic dispersion, sol, or solution of the desired radiopacifying ceramic metal oxide or a precursor organic or inorganic compound which is calcinable to the desired radiopacifying ceramic metal oxide. For brevity, the aforementioned dispersion or sol of silica will be sometimes referred to hereafter as the "silica starting material", and the aforementioned dispersion, sol, or solution of the radiopacifying ceramic metal oxide or precursor compound will sometimes be referred to hereafter as the "ceramic metal oxide starting material". The mixture of silica starting material and ceramic metal oxide starting material is dried to a solid and fired to form microparticles. Comminution may optionally be done at any stage. The microparticles can then be combined with an appropriate resin to form a composite of the invention.

Although either aqueous or organic silica starting materials can be employed in the sol-gel method just described, aqueous silica starting materials are preferred for reasons of economy. Suitable aqueous silica starting materials preferably contain colloidal silica at concentrations of about 1 to 50 weight percent, more preferably 15 to 35 weight percent. Suitable organic silica starting materials include organo-sols containing colloidal dispersions of silica in organic solvents (preferably water-miscible polar organic solvents) such as ethanol, normal or isopropyl alcohol, ethylene glycol, dimethylformamide and the various "Cellosolve" glycol ethers. The size of the colloidal silica particles in the silica starting material can vary, e.g., from 0.001 to 0.1 micrometers, preferably about 0.002 to 0.05 micrometers. Preferred sol-gel filters are those comprising zirconia and silica.

Another class of useful fillers are bioactive glasses and ceramics. Examples include Bioglass™ (U.S. Biomaterials; Alachua, Fla.); Bio-Gran™ (Orthovita; Malvern, Pa.); Cerabone A-W (Nippon Electric Glass: Japan); glasses comprising calcium oxide, silicon oxide, and phosphorous oxide; and the various phases of calcium phosphate including hydroxyapatite, monetite, brushite, and whitlockite.

Optionally, dental mill blanks may contain fluoride-releasing agents. The benefits of fluoride in reducing the incidence of caries are well established. Thus fluoride released from dental prostheses would be advantageous. Fillers that impart fluoride release include $ZnF_2$, $YbF_3$, rare-earth fluorides, $SnF_2$, $SnF_4$, $ZrF_4$, $NaF$, $CaF_2$, $YF_3$, and fluoroaluminosilicate glasses. Rare earths are the elements of atomic weights 57-71, inclusive.

The fluoride-releasing material of the present invention may be naturally occurring or synthetic fluoride minerals, fluoride glass such as fluoroaluminosilicate glass, simple and complex inorganic fluoride salts, simple and complex organic fluoride salts or combinations thereof. Optionally these fluoride sources can be treated with surface treatment agents.

Examples of the fluoride-releasing material are fluoroaluminosilicate glasses described in U.S. Pat. No. 3,814,717, which may be optionally treated as described in U.S. Pat. No. 5,332,429, the disclosures of which are both incorporated by reference herein.

The fluoride releasing material may optionally be a metal complex described by formula

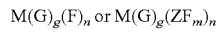

$$M(G)_g(F)_n \text{ or } M(G)_g(ZF_m)_n$$

where M represents an element capable of forming a cationic species and having a valency of 2 or more,
G is an organic chelating moiety capable of complexing with the element M,
Z is hydrogen, boron, nitrogen, phosphorus, sulfur, antimony, arsenic,
F is a fluoride atom, and
g, m and n are at least 1.

Examples of preferred M elements are the metals of groups IIA, IIIA, IVA, and transition and inner transition metal elements of the periodic table. Specific examples include $Ca^{+2}$, $Mg^{+2}$, $Sr^{+2}$, $Zn^{+2}$, $Al^{+2}$, $Zr^{+4}$, $Sn^{+2}$, $Yb^{+3}$, $Y^{+3}$, $Sn^{+4}$. Most preferably, M is $Zn^{+2}$.

Compositions of the present invention may optionally comprise at least two sources of fluoride. The first source is the fluoride-containing metal complex as described above. The second source is a fluoride-releasing fluoroaluminosilicate glass. With the use of both materials, excellent fluoride release is provided both in the initial period and over the long term use of the composition.

The mill blanks of the present invention may optionally comprise additional adjuvants suitable for use in the oral environment, including colorants, flavorants, anti-microbials, fragrance, stabilizers, and viscosity modifiers. Other suitable adjuvants include agents that impart fluorescence and/or opalescence.

As the polymer resin is initially a paste, any of the standard methods for compounding paste may be used to form the composite material. Preferably, methods which optimize mixing and minimize the incidence of material discontinuities such as voids and cracks should be instituted. For example, application of vacuum or pressure can be beneficial during any stage of compounding, forming or curing the paste. Pressure can be applied by various means, including isostatic, uniaxial, centrifugal, impact, or pressurized gas. Heat may optionally be applied at any stage. However, during curing, a uniform temperature in the sample is preferably maintained to minimize internal stresses.

During compounding and extrusion, methods that minimize and preferably eliminate material discontinuities such as voids or bubbles are preferred. Preferably the blanks of the present invention are substantially free of discontinuities in the material that are larger than about 1 millimeter. More preferably, fabrication techniques are employed such that the material is substantially free of discontinuities in the material that are larger than about 0.1 millimeter. Most preferably, blanks of the present invention are substantially free of discontinuities in the material that are larger than about 0.01 millimeter.

Blanks 20 of composite may be made in any desired shape or size, including cylinders, bars, cubes, polyhedra, ovoids, and plates. Molds 10 may be made of a variety of materials, including stainless steel, cobalt alloys, nickel alloys, aluminum alloys, plastic, glass, ceramic, or combinations thereof.

Alternatively, a variety of methods for forming and shaping the blanks into any desired configuration can be employed, such as injection molding, centrifugal casting and extrusion. During polymerization and curing, compression from springs or other means may optionally be used to reduce internal stresses. Preferably, the outer surface of the blank is smooth and non-tacky.

Curing may be performed in one or multiple stage methods. In a two-stage process, it is preferred that initial curing provide a material sufficient to sustain the forces of milling or carving. The second curing stage, therefore, can be performed on the composite after a prosthetic is milled from a blank.

Cured blocks may be attached to mounting stubs to facilitate affixation of the blank in a milling machine. Mounting stubs function as handles from which a blank is held by as it is milled by a machine.

Various means of milling the mill blanks of the present invention may be employed to create custom-fit dental prosthetics having a desired shape and morphology. The term "milling" as used herein means abrading, polishing, controlled vaporization, electronic discharge milling (EDM), cutting by water jet or laser or any other method of cutting, removing, shaping or carving material. While milling the blank by hand using a hand-held tool or instrument is possible, preferably the prosthetic is milled by machine, including computer controlled milling equipment. However, a preferred device to create a prosthetic and achieve the full benefits of the composite material of the present invention is to use a CAD/CAM device capable of milling a blank, such as the Sirona Cerec 2 machine. By using a CAD/CAM milling device, the prosthetic can be fabricated efficiently and with precision. During milling, the contact area may be dry, or it may be flushed with a lubricant. Alternatively, it may be flushed with an air or gas stream. Suitable lubricants are well known in the art, and include water, oils, glycerine, ethylene glycols, and silicones. After machine milling, some degree of finishing, polishing and adjustment may be necessary to obtain a custom fit in to the mouth and/or aesthetic appearance.

A milled dental prosthetic can be attached to the tooth or bone structure with conventional cements or adhesives or other appropriate means such as glass ionomer, resin cement, zinc phosphate, zinc polycarboxylate, compomer, or resin-modified glass. In addition, material can optionally be added to the milled prosthetic for various purposes including repair, correction, or enhancing esthetics. The additional material may be of one or more different shades or colors. The added material may be composite, ceramic, or metal. A light-cured composite is preferred.

To fabricate blanks of the present invention, the following steps are preferably performed: Compound the paste; extrude the paste into a mold; cure the paste via heat, light, microwave, e-beam or chemical cure; remove the blank from its mold and trim excess if necessary; and optionally, mount on a holder stub if necessary. A preferred method of making the dental mill blank of the present invention comprises the steps of a) mixing a paste comprising a resin and a filler, b) shaping the paste into a desired configuration, c) minimizing material discontinuities from the paste, d) curing the paste into a blank, and e) relieving internal stresses in the blank.

Optionally, where a mold is used to shape the paste, excess paste material can be trimmed from the mold. The cured past is then removed from the mold. Another optional step that can be performed in making a mill blank 20 is to mount a handle 30 onto the cured paste. Preferably, the handle is a holder stub.

Mill blanks of the present invention may be cured in a manner such that the material contains minimal internal stresses. This may be accomplished, for example, by application of pressure on the composite material during the curing process. In the alternative, the avoidance of internal stress imparted by shrinkage may be obtained by selection of mill blank components such that the overall composition exhibits little or no shrinkage during cure. A preferred curing method entails the use of light to fast cure the composite. During this fast cure, the temperature may optionally be adjusted and controlled. The fast cure technique requires a subsequent heat treatment to effectuate stress relief. Heat treatment of a cured blank requires the blank be heated for a sufficient time and at a sufficient temperature to effectively eliminate internal stresses such that the blank passes a Thermal Shock Test. Preferably, the blank is raised to a temperature of at or above Tg (glass transition temperature) of the resin component of the blank. More preferably, the blank is heated to above Tg and is maintained at that temperature for at least about one-half hour.

A preferred method of heat treatment for a cured blank is to place the blank in an oven and raise the oven temperature to about the Tg of the resin component of the blank at a rate of about, for example, 3-5° C./minute. Upon completing heat treatment, the blank is allowed to equilibrate to room temperature either by immersion into room temperature water or by slowly cooling via ambient temperature. Alternatively, the heat treatment may be accomplished by placing the blank in a preheated oven and maintaining the oven temperature at or above Tg for a sufficient time to eliminate internal stresses in the composite blank.

Another method of curing the blanks of the present invention is through a slow cure using low intensity light. In this technique, cure is accomplished over a long period of time to minimize internal stresses, such that the resulting cured blank will pass a Thermal Shock Test. Preferably, the cure takes place over a time period of about 24 hours, however it is envisioned that with proper equipment and procedure, curing times may be shorter. Progress of this cure may be evaluated by ascertaining a sample of the material at predetermined times over the cure time and evaluating progress of cure by Barcol Hardness measurement.

Other techniques may be used to relieve the stress of mill blanks of the present invention, including application of energy in a form other than heat, such as sonic or microwave energy.

A preferred method for testing the existence of residual internal stress of a composite mill blank is the Thermal Shock Test involving the use of liquid Nitrogen. Residual internal stress is undesirable because it adversely affects the structural integrity of the blank and increases the likelihood of later catastrophic failure of the blank or the ultimate prosthetic. To conduct such a test, commercially available liquid nitrogen is poured into a 250 milliliter (mL) Dewar flask. A fully cured mill blank is immersed in the liquid nitrogen until excessive bubbling subsides. If the blank explodes or experiences a large crack while immersed in the liquid nitrogen, the blank fails the Test. If the blank does not explode or did not appear to have a substantial crack, the mill blank must then be inspected for internal stress fractures (cracks). As used herein, a "crack" is defined as fissure where material has separated or broken away.

To inspect for cracks from internal stresses, the mill blank should be removed from the flask and brought to room temperature. This may be done slowly by immersing the blank in room temperature water. The blank can then be dried off and inspected for cracking. If, after up to about one hour upon the blank returning to room temperature, the blank cracks, this result also indicates a failing score for the Test.

It is essential for proper test results that the test material be free of any gross interphase between two or more materials. Thus, if a mill blank is attached to a stub, the mounting stub must be removed prior to immersing the blank in the liquid nitrogen-filled flask. Similarly, if a mill blank comprises more than one piece of material, whether it is of the same or different composition as the test material, then the material that will not ultimately be milled into a prosthetic must be removed prior to thermal shock testing.

Inspection may first be done with an unaided human eye, looking specifically for cracks that may have propagated to the blank's surface. However, while visual inspection is useful for observing cracks and discontinuities at or near the surface, it is desirable to have a nondestructive method for detecting these defects throughout the entire sample. Thus, further inspection is preferably conducted using an x-ray device that can reveal internal cracks and discontinuities. Inspection may be alternatively performed by other methods known in the art, such as ultrasonic imaging, CAT scans, NMR imaging, or eddy current measurements.

X-ray radiography is preferably used to detect cracks and discontinuities less than about 1 mm in size. This method can be used to measure the incidence of cracks and discontinuities in a blank or a batch of blanks, and furthermore as a tool for optimizing the fabrication process to minimize the incidence of cracks and discontinuities. This method is particularly useful as a quality test, wherein blanks that have detectable cracks or discontinuities are disqualified for use.

X-ray radiography comprises exposing the block to x-rays while simultaneously recording them opposite the source. Methods, materials, and equipment for such radiography are well known in the medical art. The x-ray energy and exposure times are appropriately adjusted to the material and geometries of the blanks to be inspected.

The following examples are meant to be illustrative of the invention and should not meant to limit the scope or range of the invention. Unless otherwise indicated, all parts and percentages are by weight, and all molecular weights are weight average molecular weights.

Test Methods

The following methods were used to evaluate the examples and samples.

Thermal Shock Test: Liquid Nitrogen Dip Test

A 250 mL Dewar flask (Pope Scientific, #8600) was filled with 200 mL of industrial grade liquid nitrogen. Samples (composite mill blanks) were immersed in the liquid nitrogen until excessive bubbling subsided (approximately two minutes). The blanks were removed from the liquid nitrogen and allowed to equilibrate to room temperature by immersing the blanks in room temperature water. The samples were dried off and visually inspected for cracks.

In the case of certain materials that are peculiarly sensitive to the Thermal Shock Test, special sample handling procedures may be required to assure appropriate evaluation of internal stress as compared to other factors. For example, some mill blank materials may by hydrophilic to the point of taking up atmospheric water during the cooling process of the heat treatment. The presence of such atmospheric water, particularly in a non-uniform concentration throughout the mill blank, may result in test failure even though the sample does not possess internal stress imparted by polymerization shrinkage. Maintenance of such samples in a desiccated environment (e.g. during the cooling step of the heat treatment) before the Thermal Shock Test will assure that an otherwise acceptable mill blank does not show a false failure of the Thermal Shock test. Alternative evaluation techniques may be required to show that certain materials are sufficiently free of internal stress so that they would pass the Thermal Shock Test absent the peculiarity of the materials that makes such passage impossible.

Baycol Hardness

Hardness of a cured sample was measured using a "Barber Coleman Impressor" Model GYZJ 934-1 (Barber Coleman; Rockford, Ill.).

Cuttability Value (Used for Evaluating Samples 1-10)

A Unitek™ electrical handpiece (model No. 738-151, 3M Unitek, Monrovia, Calif.) was clamped at its base such that it was level and pivoted freely about its base. Guides were placed to prevent sideways motion of the handpiece. A 151.8 g weight was suspended from the neck of the handpiece 10 centimeters (cm) from the base. The diamond rested on a mill blank secured to a platform; the cutting tool was 17.5 cm from the handpiece base.

A CEREC™ cylinder diamond 1.6 millimeters (mm) in diameter (Sirona Dental Systems; Bensheim, Germany) was secured in the handpiece. The length of contact between the diamond and the sample was 5 mm. This 5 mm diamond segment was allowed to rest on the block. The handpiece was operated at its top speed (approximately 20,000 rpm) for 60 seconds+/−1 second. The diamond and work area was flushed continuously with deionized water. At least three cuts were made on each block. A STARRETT 721 Electronic Digital Caliper (L.S. Starrett Co.; Athol, Mass.) was used to measure the height of the block adjacent to each cut and the distance from the botttom of the cut to the opposite edge of the block. The depth of the cut was calculated from the difference of these two measurements. A new diamond was used to test each block.

X-Ray Inspection

X-ray radiography was performed on a Profexray™ Rocket 300 X-ray unit (Litton Industries, Des Plaines, Ill.). 3M Diagnostic Imaging Film, Ultra Detail Plus, Rare Earth Veterinary X-ray type (3M, St. Paul, Minn.) was used to record the x-ray image; the film was developed with a 3M XT 2000 Film Processor (3M, St. Paul, Minn.). The samples were set directly on the film container, resulting in a 1:1 magnification. Settings of 300 mA, 80 kV were used; images were taken at various exposure times.

The resulting radiographs were viewed on a x-ray illuminator unit, and examined for the presence of any cracks or discontinuities, e.g. voids, pores, or knit lines.

EXAMPLES

Preparatory Example 1

A light curable resin was compounded by dissolving and mixing the following constituents:
- 0.01 pbw Ethyl 4-dimethylaminobenzoate (EDMAB)
- 0.0017 pbw camphorquinone (CPQ)
- 0.01 pbw 2-(2'-Hydroxy-5'-methylphenyl)Benzotriazole ("Tinuvin-P"; Ciba-Geigy Corp.; Hawthorne, N.Y.)
- 0.006 pbw Diphenyl Iodonium Hexafluorophosphate
- 0.4862 pbw 2,2-bis[4-(2-hydroxy-3-methacryloyloxy-propoxy)phenyl]propane (Bis-GMA)
- 0.4862 pbw triethyleneglycol dimethacrylate (TEGDMA)

Preparatory Example 2

A sol-gel derived filler was prepared as follows: 25.5 parts silica sol ("Ludox" LS: E.I duPont de Nemours & Co.) were acidified by the rapid addition of 0.255 parts concentrated nitric acid. In a separate vessel, 12.9 parts ion-exchanged zirconyl acetate (Magnesium Elektron, Inc.) were diluted with 20 parts deionized water and the resultant solution acidified with 0.255 parts concentrated nitric acid. The silica sol was pumped into the stirred zirconyl acetate solution and mixed for one hour. The stirred mixture was filtered through a 3 micrometer filter followed by a 1 micrometer filter. The filtrate was poured into trays to a depth of about 25 mm and dried at 65° C. in a forced air oven for about 35 hours (hrs). The resultant dried material was removed from the oven and tumbled through a rotary tube furnace (Harper Furnace Corp.), which was preheated to 950° C. The calcined material was comminuted in a tumbling ball mill with ¼" alumina media until an average particle size of 0.5-1.2 micrometers (as measured on a Micromeritics 5100 sedigraph) was achieved. The mill charge included 75 parts calcined material, 3 parts methanol, 1.9 parts benzoic acid, and 1.1 parts deionized water. The filler was then loaded into ceramic saggers and fired in an electric furnace (L&L Furnace Corp.) in air at 880-900° C. for approximately 8 hrs. The fired filler was then ball-milled for 4-5 hrs. The mill charge included 32 parts fired filler, 1.25 parts ethanol, and 0.3 parts deionized water. Next, the filler was passed through a 74 micrometer nylon screen in a vibratory screener (Vortisiv V/S 10010). The filler was then blended in a V-blender (Patterson-Kelly Corp.) for about 15 min.

Silane treatment was as follows: 32 parts by weight (pbw) of the filler was added to 48.94 pbw of deionized water under vigorous stirring. Trifluoroacetic acid (TFAA), 0.104 pbw, was added slowly. The pH was then adjusted to 3.0-3.3. by adding further 5 pbw increments of TFAA. Then, 3.56 pbw of silane A-174 (Union Carbide; Stamford, Conn.) was added. After stirring vigorously for 2 hrs a solution of 0.0957 pbw of calcium hydroxide and 0.30 pbw of deionized water was added and stirred an additional 5 minutes. The slurry was poured into a tray lined with a plastic sheet, and then dried in an oven set at 90° C. for 13 hours. The cakes of dried filler were crushed and passed through a 74 µm screen.

Preparatory Example 3

A commercial barium glass with a nominal average particle size of 0.7 µm (type 8235, grade UF-0.7 (Schott Glaswerke; Landshut Germany) was silane treated as follows: 2000 pbw of the glass was added to 3242 pbw of deionized water under vigorous stirring. 6.5 pbw of Trifluoroacetic acid (TFAA) was added slowly and the pH was then adjusted to 3.0-3.3. by adding further 5 pbw increments of TFAA. Then, 40.0 pbw of silane A-174 (Witco; Greenwich, Conn.) was added. After stirring vigorously for 2 hours, a solution of 5.98 pbw of calcium hydroxide and 200 g of deionized water was added and stirred an additional 5 minutes. The slurry was poured into a tray lined with a plastic sheet, and then dried in an oven set at 90° C. for 13 hours. The cakes of dried filler were crushed and passed through a 74 µm screen. The vendor literature shows a coefficient of thermal expansion (CTE) of $4.7 \times 10^{-6}$/° C., refractive index of 155.1, density of 3.04 g/cc, and a nominal composition of 30% BaO, 10% $B_2O_3$, 10% $Al_2O_3$, and 50% $SiO_2$ by weight.

Preparatory Example 4

Fumed silica, Aerosil OX50 (Degussa AG; Frankfurt, Germany), was silane treated as follows: A-174 (3.7 g) was added with stirring to 50 g of deionized water acidified to pH 3-3.3 by dropwise addition of trifluoroacetic acid. The resultant mixture was stirred at about 25° C. for 1 hour at which time 95 g of OX-50 were added to the mixture with continued stirring for 4 hours. The slurry was poured into a plastic-lined tray and dried at 35° C. for 36 hours. The silanol treated dried powder was sieved through a 74 micrometer mesh screen.

Preparatory Example 5

Silane treated quartz was prepared as follows. Quartz rock was heated to about 660° C., quenched in water, drained, then dried in a forced air oven for 16 hours at about 200° F. The quenched quartz was combined with quartz media into a mill and tumbled for about 70 hours. The charge included 99 pbw quenched quartz and 1 part methanol. The resulting particles were blended with 0.1 wt. % carbon black in a V-blender for 1 hour, then fired in an electric furnace at about 950° C. for 4 hours. The resulting particles were then passed through a 100 micrometer nylon screen, and blended in a V-blender for 30 minutes. 34.68 pbw of deionized water was adjsted to ph of 3.00-3.30 with about 0.1 pbw of TFAA. A-174 silane, 1.74 pbw, was added and then vigorously stirred for 1 hour. The quartz powder and Aerosil R972 fumed $SiO_2$ (Degussa), 62.43 and 1.01 pbw, respectively, were slowly charged to the vessel. After 90 minutes of stirring, the slurry was dried in tray at 60° C. for 18 hours and then sieved through a 70 µm screen.

Curing and Heat Treatment Samples

Paste Samples A-I

A cartridge of composite material containing 500 g of Sample 9 was placed in an air oven ("Stabil-Therm"; Blue-M Electric Co.) at 60° C. for 2 hours. Clean glass tubes, marked to fill height and plugged at the bottom end with silicone plugs, were placed in the oven at 60° C. for 1 hour.

The glass tubes were filled with the composite to the fill line and returned to the air oven for 30 minutes. The filled tubes were centrifuged (International Eqpt. Co.) at 2850 rpm for 60 minutes.

Fast Cure

Centrifuged paste contained in glass tubes were placed in an 800 mL beaker containing about 400 mL of room temperature water. The tubes were placed in the beaker evenly spaced apart, with the silicone plug at the bottom. The beaker was then placed in a Suntest Box (Suntest Accelerated Exposure Table Unit #7011, Germany) for 10 minutes. After curing, the tubes were removed from the beaker and the silicone plugs were removed. The tubes were then inverted from their original curing position and replaced in the beaker for an additional 10 minutes of curing inside the Suntest Box. The tubes were then removed from the Suntest Box and the glass tubes were separated from the cured composite blank. One blank was cut in half and inspected for discontinuties and cracks.

Slow Cure

The glass tubes containing centrifuged paste were set on a Glow-Box (Model 12.12D, 22 Watts power consumption—available from 12R Co., Cheltenham, Pa.) for 24 hours with the silicone plugs at the top. The Glow Box provided approximately 300 foot candles of light output (measured by GE Light Meter Type 213; Cleveland, Ohio). The silicone plugs were then removed. The tubes were inverted from their original curing position and replaced on the Glow Box for an additional 24 hours of curing. The tubes were then removed from the Glow Box and the glass tubes were separated from the cured composite blank. One blank was cut in half and inspected for discontinuities and cracks. Barcol hardness measurements were taken.

Post Cure

Blanks cured by both the slow and fast light cure methods above were then post-cured in a Suntest Box for 10 minutes.

Heat Treatment

Fast light cured blanks were placed in a forced air oven ("Stabil-Therm," Blue-M Electric Co.). The oven was ramped up to 100° C. at 4° C./minute. The oven temperature was maintained for 30 minutes. The oven was then shut off and the blanks were permitted to equilibrate to ambient temperature before they were tested.

Samples A through D were cured on the Glow-Box for the times shown in Table 1. Approximately 3 mm were cut off from each end. The samples were sectioned with a diamond saw into equidistant sections of approximately 10 mm thickness to produce 5 interfaces. The final dimension of each section was 14 mm×10 mm. Barcol hardness measurements with a GYZJ 934-1 hardness meter were taken in the center of each section on the obverse side of the section to the Glow-Box. An average of over three measurements were recorded.

A similar procedure for the samples made using the fast cure method (Samples E-I) was followed. Data is shown in Table 2.

TABLE 1

Slow Cure Process

| Sample | Cure Time (hrs.) | Barcol Hardness | | | | |
|---|---|---|---|---|---|---|
| | | 1 | 2 | 3 | 4 | 5 |
| A | 24 | 40 | 20 | 0 | 0 | 0 |
| B | 48 | 82 | 80 | 73 | 63 | 0 |
| C | 72 | 87 | 84 | 81 | 80 | 77 |
| D | 96 | 88 | 88 | 87 | 86 | 84 |

TABLE 2

Fast Cure Process

| Sample | Cure Time (min.) | Barcol Hardness | | | | |
|---|---|---|---|---|---|---|
| | | 1 | 2 | 3 | 4 | 5 |
| E | 5 | 0 | 0 | 0 | 0 | 0 |
| F | 10 | 0 | 0 | 0 | 0 | 0 |
| G | 15 | 48 | 51 | 50 | 52 | 55 |
| H | 20 | 84 | 85 | 81 | 84 | 84 |
| I | 25 | 88 | 90 | 91 | 89 | 91 |

Forty-one samples were made using the same procedure described above for making Samples A-I. Eight samples were slow cured, twelve were fast cured, and the remaining twenty-one samples were fast cured and heat-treated. All forty-one samples tested using the Thermal Shock Test.

TABLE 3

| | | Results of Thermal Shock Test | |
|---|---|---|---|
| Cure Mode | Heat Treat | Pass | Fail |
| Slow | No | 8 | 0 |
| Fast | No | 0 | 12 |
| Fast | Yes | 21 | 0 |

Sample Preparation

Composite Paste Samples 1-8 were prepared by charging fillers and resin to a plastic beaker and then stirring and kneading these constituents into a paste with a flattened glass rod.

TABLE 4

| Sample No. | Amount of Preparatory Example 1 Resin (pbw) | Type and Amount of Filler (pbw) |
|---|---|---|
| 1 | 30 | 70, Preparatory Example 2 |
| 2 | 30 | 70, Preparatory Example 3 |
| 3 | 30 | 70, Preparatory Example 5 |
| 4 | 40 | 60, Preparatory Example 4 |
| 5 | 20 | 80, Preparatory Example 2 |
| 6 | 20 | 80, Preparatory Example 5 |
| 7 | 40 | 60, Preparatory Example 3 |
| 8 | 50 | 50, Preparatory Example 4 |
| 9* | 14.7 | 85.3 Preparatory Example 2 |

*Sample No. 9 was compounded in a double planetary mixer.

A Comparative Sample 10 was made from commerically available Vita Mark II A3C/I12 Restorative (Vita Zahnfabrik, Bad Sackingen, Germany). When possible, pastes were compounded in a range containing filler from 70 to 80 weight percent. With the Preparatory Example 3 filler, Schott 8235 Glass, the paste became dry and crumbly at about 73-76% by weight of filler. With the Preparatory Example 4 filler, Aerosil OX50, the paste became far too thick to mix by hand when the filler content was greater than about 60% by weight.

Loading, Curing and Heat Treatment of Samples 1-9

The paste was filled into plastic cuvets and then compressed manually with a stainless steel plunger. The filled cuvets were then placed in a Kulzer™ Dentacolor™ XS Curing Unit™ (Heraueus Kulzer; Irvine, Calif.) and cured for 90 seconds on each long side. Total curing time was 360 seconds. The plastic cuvet was then broken off to produce a cured mill block of approximately 10×10 mm cross section by 3-4 cm long. Blocks were heat treated in an oven by placing them in a cool oven. The oven was then heated to 10° C. and maintained at that temperature for one hour. The oven was then turned off and the samples were allowed to cool in the oven to room temperature.

Each sample was evaluated for cuttability and Barcol Hardness. Barcol Hardness of the composite blanks was tested with a Barber Coleman Impressor Model GYZJ 934-1 (Barber Coleman; Rockford, Ill.). An average of the three readings was recorded.

Cuttability is calculated by the following equation, percent increase compared to Sample 8 equals [(Cuttability−Cuttability of Sample 8)/Cuttability of Sample 8] multiplied by 100.

TABLE 5

| Sample No. | Filler or Product | Filler wt % | Cuttability: Avg Depth (mm) | % Increase of Cuttability Compared to Sample 8 | Barcol- avg |
|---|---|---|---|---|---|
| 1 | Sol-gel | 70 | 0.93 | 70 | 79.3 |
| 2 | Glass | 70 | 0.71 | 29 | 86.0 |
| 3 | Quartz | 70 | 0.72 | 32 | 77.3 |
| 4 | Fumed Silica | 60 | 0.56 | 2 | 78.3 |
| 5 | Sol-gel | 80 | 1.24 | 127 | 85.0 |
| 6 | Quartz | 80 | 1.45 | 166 | 80.3 |
| 7 | Glass | 60 | 1.05 | 93 | 75.5 |
| 8 | Fumed Silica | 50 | 0.55 | 0 | 75.0 |
| 9 | Sol-Gel | 85.3 | 2.01 | 268 | 89.5 |
| Comparative 10 | Vita Mark II A3C/I12 (no heat treatment) | | 0.83 | 44 | — |

Sample 11

3M F2000 shade A2 (3M Co.; St. Paul, Minn.), fluoride-releasing material, was extruded into a cuvet to about ¾ full. The filled cuvet was placed standing vertically in a Hanau Sun-Test box with a xenon lamp and exposed to light for 30 min. The cuvet was rotated lengthwise and exposed to light another 30 min. The cured block was heat treated in a Despatch oven at 100° C./60 min., then allowed to cool in the oven.

X-Ray Analysis of Samples

Examples X1-X8 were fabricated in the same way as Samples E-I except that they were centrifuged at 2700 RPM, and light cured for 30 minutes immersed in water; and not heat-treated.

Examples X9-X12 were fabricated in the same way as Sample E-I except that they were centrifuged at 2700 RPM, and light cured for 41 minutes immersed in water; and heat-treated in the same way as samples 1-9.

Examples X13-X22 were fabricated in the same way as Samples E-I except that they were centrifuged at 2700 RPM, and light cured for 30 minutes immersed in water; and heat-treated in the same way as samples 1-9.

Example X23 was fabricated in the same way as Samples E-I except that it was centrifuged at 2400 RPM, and light cured for 30 minutes immersed in water; and heat-treated in the same way as samples 1-9.

Examples X24-28 are commercial Vita Mark II Vitablocs.

Examples X29-X32 were fabricated in the same way as Samples A-D except that the paste was heated to 45° C. for filling.

TABLE 6

| Sample # | Exposure time (sec) | Observation |
|---|---|---|
| X1 | 1/30 | many pores, ~0.5-2 mm |
| X2 | 1/30 | no cracks or other discontinuities visible |
| X3 | 1/30 | no cracks or other discontinuities visible |
| X4 | 1/30 | no cracks or other discontinuities visible |
| X5 | 1/30 | several pores 1-4 mm |
| X6 | 1/30 | no cracks or other discontinuities visible |
| X7 | 1/30 | no cracks or other discontinuities visible |
| X8 | 1/30 | no cracks or other discontinuities visible |
| X9 | 1/30 | no cracks or other discontinuities visible |
| X10 | 1/30 | no cracks or other discontinuities visible |
| X11 | 1/30 | large pit at end open to surface |
| X12 | 1/30 | large pit at end open to surface |
| X13 | 1/30 | flat pores, about 0.1 mm thick × 3 mm long |
| X14 | 1/30 | flat pores, about 0.1 mm thick × 3 mm long |
| X15 | 1/30 | flat pores, about 0.1 mm thick × 3 mm long |
| X16 | 1/30 | flat pores, about 0.1 mm thick × 3 mm long |
| X17 | 1/30 | no cracks or other discontinuities visible |
| X18 | 1/30 | no cracks or other discontinuities visible |
| X19 | 1/30 | no cracks or other discontinuities visible |
| X20 | 1/30 | no cracks or other discontinuities visible |
| X21 | 1/30 | flat pores, about 0.1 mm thick × 3 mm long |
| X22 | 1/30 | flat pores, about 0.1 mm thick × 3 mm long |
| X23 | 1/30 | one pore ~3 mm; one crack ~5 mm long |
| X24 | 1/30 | no cracks or other discontinuities visible |
| X25 | 1/30 | no cracks or other discontinuities visible |
| X26 | 1/30 | no cracks or other discontinuities visible |
| X27 | 1/30 | no cracks or other discontinuities visible |
| X28 | 1/30 | no cracks or other discontinuities visible |
| X29 | 1/30 | no cracks or other discontinuities visible |
| X30 | 1/30 | narrow longitudinal crack 0.1 mm wide top to bottom |
| X31 | 1/30 | small crack ~0.1 mm wide |
| X32 | 1/30 | small crack <0.1 mm wide |

What is claimed:

1. A dental mill blank suitable for the oral environment prepared by a method comprising:
   mixing a paste comprising a resin and a filler,
   adding a fluoride releasing material to the paste,
   shaping the paste into a desired configuration,
   minimizing material discontinuities from the paste,
   curing the paste into a blank, and
   heating the blank to a temperature at or above the Tg of the resin for a time sufficient to relieve internal stresses in the blank,
   wherein the cured mill blank, when immersed in liquid nitrogen for about two minutes, does not explode and no cracks are observed upon visual inspection, and
   wherein the dental mill blank is suitable for making a dental prosthetic selected from the group consisting of onlays, full crowns, partial crowns, bridges, implants, and posts.

2. A dental prosthetic suitable for the oral environment prepared by a method comprising:
   providing a dental mill blank comprising a cured resin and a filler;
   heating the dental mill blank to a temperature at or above the Tg of the resin for a time sufficient to relieve internal stresses in the blank; and
   carving the heated blank into a desired shape and morphology for a dental prosthetic,
   wherein the dental prosthetic, when immersed in liquid nitrogen for about two minutes, does not explode and no cracks are observed upon visual inspection, and
   wherein the dental prosthetic is selected from the group consisting of onlays, full crowns, partial crowns, bridges, implants, and posts.

3. The dental prosthetic of claim 2 wherein the method further comprises milling the blank on a milling machine.

4. The dental prosthetic of claim 2 wherein the method further comprises attaching the carved blank to a tooth or bone structure.

5. The dental prosthetic of claim 2 wherein the method further comprises attaching a handle to the cured mill blank.

6. The dental prosthetic of claim 2 wherein the cured resin is derived from a resin selected from the group consisting of a free radically curable monomer, a free radically curable oligomer, a free radically curable polymer, a cationically curable monomer, a cationically curable oligomer, a cationically curable polymer, and combinations thereof.

7. The dental prosthetic of claim 6 wherein the cured resin is an acrylate or methacrylate resin.

8. The dental prosthetic of claim 6 wherein the cured resin is an epoxy resin.

9. A dental prosthetic suitable for the oral environment prepared by a method comprising:
   mixing components comprising a resin and a filler;
   shaping the mixture into a desired configuration;
   minimizing material discontinuities;
   curing the mixture into a blank;
   heating the blank to a temperature at or above the Tg of the resin for a time sufficient to relieve internal stresses in the blank; and
   carving the heated blank into a desired shape and morphology for the dental prosthetic,
   wherein the dental prosthetic, when immersed in liquid nitrogen for about two minutes, does not explode and no cracks are observed upon visual inspection, and
   wherein the dental prosthetic is selected from the group consisting of onlays, full crowns, partial crowns, bridges, implants, and posts.

10. The dental prosthetic of claim 9 wherein carving comprises carving by a milling machine.

11. The dental prosthetic of claim 9 wherein a contact area between the blank and milling machine is dry or flushed with a lubricant.

12. The dental prosthetic of claim 9 wherein the method further comprises attaching the carved blank to a tooth or bone structure.

13. The dental prosthetic of claim 9 wherein the method further comprises attaching a handle to the cured mill blank.

14. The dental prosthetic of claim 9 wherein curing comprises initiation of polymerization by one or more of heat, light, radiation, e-beam, microwave, or chemical reaction.

15. The dental prosthetic of claim 9 wherein the resin is selected from the group consisting of a free radically curable monomer, a free radically curable oligomer, a free radically curable polymer, a cationically curable monomer, a cationically curable oligomer, a cationically curable polymer, and combinations thereof.

16. The dental prosthetic of claim 9 wherein the resin is an acrylate or methacrylate resin.

17. The dental prosthetic of claim 9 wherein the resin is an epoxy resin.

18. The dental prosthetic of claim 9 wherein the method further comprises application of pressure or vacuum during one or more of the steps of making the heated blank.

19. The dental prosthetic of claim 18 wherein the applied pressure comprises one or more of isostatic pressure, uniaxial pressure, centrifugal pressure, impact pressure, or pressurized gas.

20. The dental prosthetic of claim 9 wherein the components further comprise an initiator system selected from the group consisting of free radical-generating thermal initiators, thermal redox initiators, photoinitiators, and dual initiation systems.

* * * * *

UNITED STATES PATENT AND TRADEMARK OFFICE
CERTIFICATE OF CORRECTION

PATENT NO. : 8,317,516 B2 Page 1 of 2
APPLICATION NO. : 12/914433
DATED : November 27, 2012
INVENTOR(S) : Richard P Rusin It is certified that error appears in the above-identified patent and that said Letters Patent is hereby corrected as shown below:

<u>Title Page 2, Item (56) Column 2 (Other Publications)</u>
Line 15            Delete "Weinburg, ed.," and insert -- Weinberg, ed., --, therefor.

<u>In the Specifications</u>

<u>Column 2</u>
Line 45            Delete "blanks" and insert -- blanks. --, therefor.

<u>Column 3</u>
Line 24            Delete "blanks" and insert -- blanks. --, therefor.

<u>Column 4</u>
Line 17            Delete "130 gaper" and insert -- 130 g/l per --, therefor.
Line 52            Delete "blanks" and insert -- blanks. --, therefor.

<u>Column 6</u>
Line 39            After "citraconic acid," delete "acid,".

<u>Column 7</u>
Line 56            Delete "tetramethyl-1.2" and insert -- tetramethyl-1,2 --, therefor.

<u>Column 8</u>
Line 12            Delete "Weinburg, Ed.," and insert -- Weinberg, Ed., --, therefor.
Lines 66-67        Delete "dimethylaminophenethanol," and insert
                   -- dimethylaminophenylethanol, --, therefor.

Signed and Sealed this
Eleventh Day of June, 2013

Teresa Stanek Rea
*Acting Director of the United States Patent and Trademark Office*

CERTIFICATE OF CORRECTION (continued)
U.S. Pat. No. 8,317,516 B2

In the Specifications

Column 9
Line 7 — Delete "N-methylpyrollidone," and insert -- N-methylpyrrolidone, --, therefor.

Column 12
Line 23 — Delete "HA," and insert -- IIA, --, therefor.
Line 25 — Delete "Al$^{+2}$," and insert -- Al$^{+3}$, --, therefor.

Column 16
Line 4 — Delete "Baycol" and insert -- Barcol --, therefor.
Line 28 — Delete "botttom" and insert -- bottom --, therefor.

Column 17
Line 28 — Delete "3.0-3.3. by" and insert -- 3.0-3.3 by --, therefor.
Line 46 — Delete "3.0-3.3. by" and insert -- 3.0-3.3 by --, therefor.

Column 18
Line 16 (Approx.) — Delete "adjsted" and insert -- adjusted --, therefor.
Line 50 — Delete "discontinuties" and insert -- discontinuities --, therefor.
Line 54 — Delete "12R Co.," and insert -- I2R Co., --, therefor.

Column 20
Line 15 (Approx.) — Delete "commerically" and insert -- commercially --, therefor.
Line 25 — Delete "cuvets" and insert -- cuvettes --, therefor.
Line 27 — Delete "cuvets" and insert -- cuvettes --, therefor.
Line 28 — Delete "(Heraueus" and insert -- (Heraeus --, therefor.
Line 30 — Delete "cuvet" and insert -- cuvette --, therefor.
Lines 33-34 — Delete "10°C." and insert -- 100°C. --, therefor.
Line 65 — Delete "cuvet" and insert -- cuvette --, therefor.
Line 66 — Delete "cuvet" and insert -- cuvette --, therefor.

Column 21
Line 1 — Delete "cuvet" and insert -- cuvette --, therefor.
Line 22 — Delete "Vitablocs." and insert -- Vitablocks. --, therefor.